(12) United States Patent
Vargo

(10) Patent No.: US 12,207,797 B2
(45) Date of Patent: Jan. 28, 2025

(54) LARYNGOSCOPE

(71) Applicant: Bradley J. Vargo, Kirtland, OH (US)

(72) Inventor: Bradley J. Vargo, Kirtland, OH (US)

(73) Assignee: Bradley J. Vargo, Kirtland, OH (US)

(*) Notice: Subject to any disclaimer, the term of this patent is extended or adjusted under 35 U.S.C. 154(b) by 1066 days.

(21) Appl. No.: 17/137,560

(22) Filed: Dec. 30, 2020

(65) Prior Publication Data

US 2021/0137376 A1     May 13, 2021

Related U.S. Application Data

(63) Continuation-in-part of application No. 17/004,475, filed on Aug. 27, 2020, now Pat. No. 12,029,396.
(Continued)

(51) Int. Cl.
*A61B 1/267*      (2006.01)
*A61B 1/00*      (2006.01)
(Continued)

(52) U.S. Cl.
CPC .......... *A61B 1/267* (2013.01); *A61B 1/00016* (2013.01); *A61B 1/00029* (2013.01);
(Continued)

(58) Field of Classification Search
CPC . A61B 1/267; A61B 1/00016; A61B 1/00029; A61B 1/00045; A61B 1/05;
(Continued)

(56) References Cited

U.S. PATENT DOCUMENTS

| 2,354,471 A | 7/1944 | Macintosh |
| 2,646,036 A | 7/1953 | Allyn et al. |

(Continued)

FOREIGN PATENT DOCUMENTS

| WO | WO 03/075979 A2 | 9/2003 |
| WO | WO 2019/032459 A1 | 2/2019 |
| WO | WO 2021/041626 A1 | 3/2021 |

OTHER PUBLICATIONS

Baker, Paul A. et al., "*Visual Acuity During Direct Laryngoscopy at Different Illuminance Levels*" www.anesthesia-analgesia.org, Feb. 2013, vol. 116, No. 2, pp. 343-350.
(Continued)

*Primary Examiner* — Eduardo C Robert
*Assistant Examiner* — Christina Negrellirodriguez
(74) *Attorney, Agent, or Firm* — Lippes Mathias LLP

(57) ABSTRACT

A laryngoscope has a handle including an electromagnetic coil, and a blade, and one or more electrical components including at least one of a light emitting diode (LED) and/or an image sensor. The one or more electrical components are operatively connected to be powered by electrical current induced in the electromagnetic coil by near field magnetic induction. A laryngoscope system includes the laryngoscope and a radio frequency (RF) power generator configured to induce the electrical current in the electromagnetic coil of the laryngoscope. The RF power generator may include a transmitting coil resonant at the same RF frequency as the electromagnetic coil of the laryngoscope. In a direct observation laryngoscope embodiment, the one or more electrical components includes the LED. In a video laryngoscope embodiment, the one or more electrical components includes the image sensor and a radio transmitter to transmit video acquired by the image sensor.

19 Claims, 4 Drawing Sheets

Related U.S. Application Data

(60) Provisional application No. 62/894,175, filed on Aug. 30, 2019.

(51) Int. Cl.
  *A61B 1/05* (2006.01)
  *A61B 1/06* (2006.01)
  *H01F 38/14* (2006.01)
  *H02J 50/10* (2016.01)
  *H02J 50/20* (2016.01)

(52) U.S. Cl.
  CPC ............ *A61B 1/00045* (2013.01); *A61B 1/05* (2013.01); *A61B 1/0684* (2013.01); *H01F 38/14* (2013.01); *H02J 50/10* (2016.02); *H02J 50/20* (2016.02)

(58) Field of Classification Search
  CPC ........ A61B 1/0684; H02J 50/10; H02J 50/20; H01F 38/14
  See application file for complete search history.

(56) References Cited

U.S. PATENT DOCUMENTS

| | | | |
|---|---|---|---|
| 4,678,608 | A | 7/1987 | Dugliss |
| 4,717,511 | A | 1/1988 | Koroscil |
| 5,277,173 | A | 1/1994 | Cantele |
| 9,459,326 | B2 | 10/2016 | Mcgrath et al. |
| 9,559,553 | B2 | 1/2017 | Bae |
| 10,122,212 | B2 | 11/2018 | Jeong et al. |
| 10,205,349 | B2 | 2/2019 | Cho et al. |
| 10,410,787 | B2 | 9/2019 | Jeong et al. |
| 10,460,883 | B2 | 10/2019 | Jeong et al. |
| 10,516,446 | B2 | 12/2019 | Jeong et al. |
| 10,778,036 | B2 | 9/2020 | Jeong |
| 2004/0122292 | A1 | 6/2004 | Dey et al. |
| 2005/0065496 | A1 | 3/2005 | Simon et al. |
| 2005/0187434 | A1 | 8/2005 | Dey et al. |
| 2009/0209816 | A1* | 8/2009 | Gunther Nielsen ........ A61B 1/00006 600/118 |
| 2010/0312059 | A1 | 12/2010 | Megrath |
| 2011/0301414 | A1 | 12/2011 | Hotto et al. |
| 2014/0160261 | A1 | 6/2014 | Miller et al. |
| 2016/0338581 | A1* | 11/2016 | McGrath ........... A61M 16/0488 |
| 2017/0258311 | A1 | 9/2017 | Merz et al. |
| 2017/0367567 | A1 | 12/2017 | Swift |
| 2018/0090994 | A1* | 3/2018 | Jeong ........................ G05F 3/00 |
| 2018/0152053 | A1 | 5/2018 | Jeong et al. |
| 2018/0168433 | A1 | 6/2018 | Meyer et al. |
| 2019/0200556 | A1 | 7/2019 | Shelton, IV |
| 2019/0229559 | A1 | 7/2019 | Boccoleri et al. |

OTHER PUBLICATIONS

Tousigant, Guy et al., "*Equipment—Light intensity and area of illumination provided by various laryngoscope blades*" Canadian Journal of Anesthesia, 1994, 41:0, pp. 865-869.

Aslan, Kadir et al., "*Metal-Enhanced Chemiluminescence: Advanced Chemiluminescence Concepts for the 21st Century*", Chemical Society Reviews, Jun. 10, 2009, doi: 10.1039/b807498b.

Ray, Krishanu et al., "*Aluminum Nanostructured Films as Substrates for Enhanced Fluorescence in the Ultraviolet-Blue Spectral Region*", Analytical Chemistry, Aug. 8, 2007, doi: 10.1021/ac0713631.

Article titled "*Microbiology with Aquaspark™: A Novel Tool for Enzymatic Activity Detection*", Biosynth Chemistry & Biology / Nemis Technologies, Product Mini Reviews 2018.

Scholz, Anette, et al., "Minimum and optimum light output of Macintosh size 3 laryngoscopy blades: a manikin study" https://doi.org/10.1111/j.1365-2044.2006.04912.x, Jan. 10, 2007.

Sherman, Jodi, "*Reusable vs. Disposable Laryngoscopes*", https://apsf.org/newsletter/february-2019, Feb. 2019.

Storz, Karl, "*C-MAC® S Video Laryngoscope and Laryngobloc Cold Light Laryngoscope*", EndoWorld® AN 13 6.1, Jan. 2018.

Janeway, Henry H., "*Intra-Trachael Anesthesia from the Standpoint of the Nose, Throat and Oral Surgeon with Description of a New Instrument for Catheterizing the Trachea*", From the Department of Experimental Surgery of New York University and Bellevue Hospital Medical College, pp. 1082-1090, Date Unknown.

Datasheet titled "*SCHOTT® Image Conduit*", Date Unknown.

International Search Report mailed Sep. 23, 2021 for International application No. PCT/US2021/01620.

Written Opinion of the International Searching Authority mailed Sep. 23, 2021 for International application No. PCT/US2021/01620.

Weiser, Thomas G. et al., article titled "*An estimation of the global volume of surgery: a modelling strategy based on available data*", www.thelancet.com, published online Jun. 25, 2008, DOI:10.1016/S0140-6736(08)60878-8.

American Association of Nurse Anesthetists' Publication titled "*Certified Registered Nurse Anesthetists Fact Sheet*", publication updated Feb. 1, 2021.

Whitener, Dewayne, Publication titled "*The Cost of Reusable vs. Single-Use Laryngoscopes*", Southeast Health, Aug. 8, 2012.

ON Semiconductor, publication titled "*Product Overview ARX3A0: CMOS Image Sensor, Ultra-Low-Power, 560×560, 360 fps*", publication date unknown.

Consumer and Clinical Radiation Protection Bureau Environmental and Radiation Health Sciences Directorate Healthy Environments and Consumer Safety Branch Health Canada, publication titled "*Limits of Human Exposure to Radiofrequency Electromagnetic Energy in the Frequency Range from 3 KHZ to 300 GHZ*", Cat .: H129-48/2015E-PDF Isbn: 978-0-660-02466-0 Pub .: 150021, published Jun. 2015.

Tiikkaja, Maria et al., article titled "*Electromagnetic interference with cardiac pacemakers and implantable cardioverter-defibrillators from low-frequency electromagnetic fields in vivo*", European Society of Cardiology, Europace (2013) 15, 388-394, doi:10.1093/europace/eus345, published online Nov. 1, 2012.

Carroll, Aaron et al., Article titled "*An Analysis of Power Consumption in a Smartphone*", USENIXATC'10: Proceedings of the 2010 USENIX conference on USENIX Annual Technical Conference, Jun. 2010.

Cheung, Ka Wai et al., article titled "*Minimal Illumination for Direct Laryngoscopy and Intubation in Different Ambient Light Settings*", Society for Academic Emergency Medicine, vol. 17, No. 1, Jan. 2010.

Liu, Xun et al., article titled "*Optimal Design of a Hybrid Winding Structure for Planar Contactless Battery Charging Platform*", IEEE Transactions on Power Electronics, vol. 23, No. 1, Jan. 2008.

Anderson, K.J. et al., article titled "*The effect of single use laryngoscopy equipment on illumination for tracheal intubation\**", presented at the Difficult Airway Society, Nov. 23, 2001.

Waffenschmidt, E. et al., Abstract for article titled "*Limitation of inductive power transfer for consumer applications*", Power Electron. Appl. 2009, 13th European Conference on Power Electronics and Applications, 2009, p. 1-10.

Tseng, Ryan et al., Article titled "*Introduction to the Alliance for Wireless Power Loosely-Coupled Wireless Power Transfer System Specification Version 1.0*", 2013 IEEE, IEEE Wireless Power Transfer Conference 2013, Technologies, Systems and Applications, May 15-16, 2013, Perugia, Italy. pp. 79-83, DOI: 10.1109/WPT.2013.6556887.

Kurs, A. et al., article titled "*Wireless Power Transfer via Strongly Coupled Magnetic Resonances*", Science, sciencemag.org, vol. 317, Jul. 6, 2007.

Imura, Takehiro, et al., Abstract for article titled "*Basic experimental study on helical antennas of wireless power transfer for Electric Vehicles by using magnetic resonant couplings*", IEEE Vehicle Power and Propulsion Conference, pp. 936-940, published 2009.

Nini, Puqi et al., Abstract for article titled "*Genetic algorithm based coil system optimization for wireless power charging of electric*

(56) References Cited

OTHER PUBLICATIONS

*vehicles*", IEEE Transportation Electrification Conference and Expo (ITEC) Jun. 16-19, 2013, DOI:10.1109/ITEC.2013.6574509.
Sherman, Jodi et al., Article titled "*Balancing Infection Control and Environmental Protection as a Matter of Patient Safety: The Case of Laryngoscope Handles*", Anesthesia-Analgesia, Jan. 9, 2018.
Skilton, R.W.P. et al., Article titled "*A study of the brightness of laryngoscope light*", Anaesthesia, vol. 51, pp. 667-672.
Pamphlet titled IEEE, Standards Interpretation for IEEE Std. C95.1™—2005 IEEE Standard for Safety Levels with Respect to Human Exposure to Radio Frequency Electromagnetic Fields, 3kHz to 300 GHz, published Oct. 2011.
Letter dated Apr. 24, 2019 to Julius Knapp from Department of Health and Human Services, Food and Drug Administration.
Yilmaz, Murat et al. "Review of Battery Charger Topologies, Charging Power Levels, and Infrastructure for Plug-In Electric and Hybrid Vehicles" IEEE Transactions on Power Electronics, vol. 28, No. 5, May 2012.

\* cited by examiner

LARYNGOSCOPE

This application is a continuation-in-part (CIP) of U.S. application Ser. No. 17/004,475 filed Aug. 27, 2020 and titled "LARYNGOSCOPE" which claims the benefit of U.S. Provisional Application No. 62/894,175 filed Aug. 30, 2019 and titled "LARYNGOSCOPE". U.S. application Ser. No. 17/004,475 filed Aug. 27, 2020 and titled "LARYNGOSCOPE" is incorporated herein by reference in its entirety. U.S. Provisional Application No. 62/894,175 filed Aug. 30, 2019 and titled "LARYNGOSCOPE" is incorporated herein by reference in its entirety.

BACKGROUND

The following relates to laryngoscopy arts, tracheal intubation arts, and the like.

A laryngoscope is a device used by an anesthesiologist or other medical professional in order to look inside a patient's pharynx to view the larynx, vocal cords, and glottis. A common use of a laryngoscope is during tracheal intubation, where a laryngoscope is used to visually monitor insertion of a tracheal tube to ensure the tube is inserted into the tracheal opening, rather than into the neighboring esophageal opening. A typical commercially available laryngoscope includes a handle on which a straight or curved laryngoscope blade is mounted, with the blade typically oriented roughly perpendicularly to the handle. The laryngoscope blade is inserted into the patient's mouth and is used to move the tongue and epiglottis aside to provide an unimpeded view of the glottis. In a tracheal intubation procedure, this maneuver also provides an unobstructed path for insertion of a tracheal tube into the tracheal opening. A lamp is mounted on the blade (or in the handle, with a light conduit directing the light out and along the blade) and is powered by a battery disposed in the handle in order to provide illumination of the larynx and glottis. Macintosh, U.S. Pat. No. 2,354,471 issued Jul. 25, 1944 discloses a curved blade design commonly known as a Macintosh blade. However, other types of laryngoscope blades such as straight blades (for example, a Miller blade, see, e.g. Swift, U.S. Pub. No. 2017/0367567 A1) are also known and used for various laryngoscopy tasks. A given laryngoscope blade shape may be optimized for anatomical particularities of a particular class of patients, and/or for a particular laryngoscopy procedure. For example, some laryngoscope blades incorporate a tube guide for guiding a tracheal tube. In a variant approach, laryngoscope designs that replace the battery with a chemiluminescent light source are described in Cantele, U.S. Pat. No. 5,277,173 and Weinmann, Int'l. Pub. WO 2019/032459 A1.

Video laryngoscopes have also been developed, that employ a video camera to image the larynx and tracheal opening. See, e.g. McGrath, U.S. Pub. No. 2016/0338581 A1; Merz et al., U.S. Pub. No. 2017/0258311 A1. Video laryngoscopes have been commercialized, e.g. the Glide-Scope® line of laryngoscopes available from Verathon Inc. Video laryngoscopes may have a separate video monitor, or may have a video monitor incorporated into the handle, or as some other integral part of the video laryngoscope. Video laryngoscopes utilize either a battery or an external power source, and can be particularly useful for more challenging tracheal intubation procedures. Most commonly used when direct laryngoscopy is expected to be potentially difficult, video indirect visualization of the larynx can be accomplished with exaggerated curved angles of the blade component with installed video related image acquisition, such as a lens and/or fiberoptics and distal blade light source. This has improved success of first attempt intubations and made it possible for others to observe the procedure. Such equipment has disadvantages such as attached wires for powering the video, remote or mounted video displays that are typically non-disposable as infectious waste, and relatively high cost to produce and maintain reusable laryngoscopic instruments.

An issue that can arise in laryngoscope procedures is the potential for unwarranted medical malpractice claims. In some instances, a patient may make a claim against the anesthesiologist alleging that a tracheal intubation procedure caused dental or oral damage. In spite of adequate pre-evaluation, it can be difficult to demonstrate that the damage was a pre-existing condition, or occurred during the medical procedure subsequent to intubation. As the cost of the liability claim is typically relatively low, insurance companies often settle such claims to avoid the cost of litigation. However, this can reflect negatively on the anesthesiologist, and may lead to a rate increase for liability insurance. Hence, it would be desirable to reduce the incidence of filed claims and resulting settlements.

Certain improvements are disclosed herein.

BRIEF SUMMARY

In accordance with some illustrative embodiments disclosed herein, a video laryngoscope comprises: a handle; a laryngoscope blade having a proximal end connected with the handle and a distal end that is distal from the handle; a chemiluminescent light source disposed inside the handle; one or more photovoltaic cells disposed inside the handle and optically coupled with the chemiluminescent light source to convert chemiluminescence emitted by the chemiluminescent light source into electrical power; and an image sensor disposed on the laryngoscope blade or in the handle and configured to image the glottis of an associated patient when the distal end of the laryngoscope blade operatively engages the tongue of the associated patient. The image sensor is powered by the electrical power produced by the one or more photovoltaic cells.

In accordance with some illustrative embodiments disclosed herein, a laryngoscope comprises: a handle; a laryngoscope blade having a proximal end connected with the handle and a distal end that is distal from the handle; an electrical power device disposed inside the handle and configured to emit electrical power; and at least one of a light emitting diode (LED) and/or an image sensor disposed on or in the laryngoscope and arranged to illuminate and/or view the glottis of an associated patient when the laryngoscope blade operatively engages the tongue of the associated patient. The LED and/or image sensor is powered by the electrical power emitted by the electrical power device. The electrical power device comprises a chemiluminescent light source disposed inside the handle, and one or more photovoltaic cells disposed inside the handle and optically coupled with the chemiluminescent light source to convert chemiluminescence emitted by the chemiluminescent light source into the electrical power.

In accordance with some illustrative embodiments disclosed herein, a laryngoscope comprises: a handle; a laryngoscope blade having a proximal end connected with the handle and a distal end that is distal from the handle; an electrical power device disposed inside the handle and configured to emit electrical power; and at least one of a light emitting diode (LED) and/or an image sensor disposed on or in the laryngoscope and arranged to illuminate and/or view the glottis of an associated patient when the laryngoscope blade operatively engages the tongue of the associated patient. The LED and/or image sensor is powered by the electrical power emitted by the electrical power device. The electrical power device comprises an electromagnetic coil disposed inside the handle to emit the electrical power comprising an electrical current induced in the-electromagnetic coil.

In accordance with some illustrative embodiments disclosed herein, a system is disclosed for recording tracheal intubation procedures performed by a plurality of video laryngoscopes. The system comprises a server computer and at least one user interface device. The server computer is configured to connect with a video laryngoscope of the plurality of video laryngoscopes and to receive video from the connected video laryngoscope and to process the video by operations including performing face identification on the video and removing any frames of the video depicting a human face to generate anonymized video, tagging the anonymized video with a video recording timestamp and at least one of (i) a surgical location and/or (ii) or an anesthesiologist identifier, and storing the anonymized video with the tags on a non-transitory storage medium. At least one user interface device is configured to retrieve selected anonymized video from the non-transitory storage medium. The selected anonymized video is selected on the basis of the video recording timestamp and the surgical location and/or anesthesiologist identifier.

In accordance with some illustrative embodiments disclosed herein, A laryngoscope has a handle including an electromagnetic coil, and a blade, and one or more electrical components including at least one of a LED and/or an image sensor. The one or more electrical components are operatively connected to be powered by electrical current induced in the electromagnetic coil by near field magnetic induction. A laryngoscope system includes the laryngoscope and a radio frequency (RF) power generator configured to induce the electrical current in the electromagnetic coil of the laryngoscope. The RF power generator may include a transmit electromagnetic coil resonant at the same RF frequency as the electromagnetic coil of the laryngoscope. In a direct observation laryngoscope embodiment, the one or more electrical components includes the LED. In a video laryngoscope embodiment, the one or more electrical components includes the image sensor and a radio transmitter to transmit video acquired by the image sensor.

BRIEF DESCRIPTION OF THE DRAWINGS

Any quantitative dimensions shown in the drawing are to be understood as non-limiting illustrative examples. Unless otherwise indicated, the drawings are not to scale; if any aspect of the drawings is indicated as being to scale, the illustrated scale is to be understood as non-limiting illustrative example.

DETAILED DESCRIPTION

Figure 1:
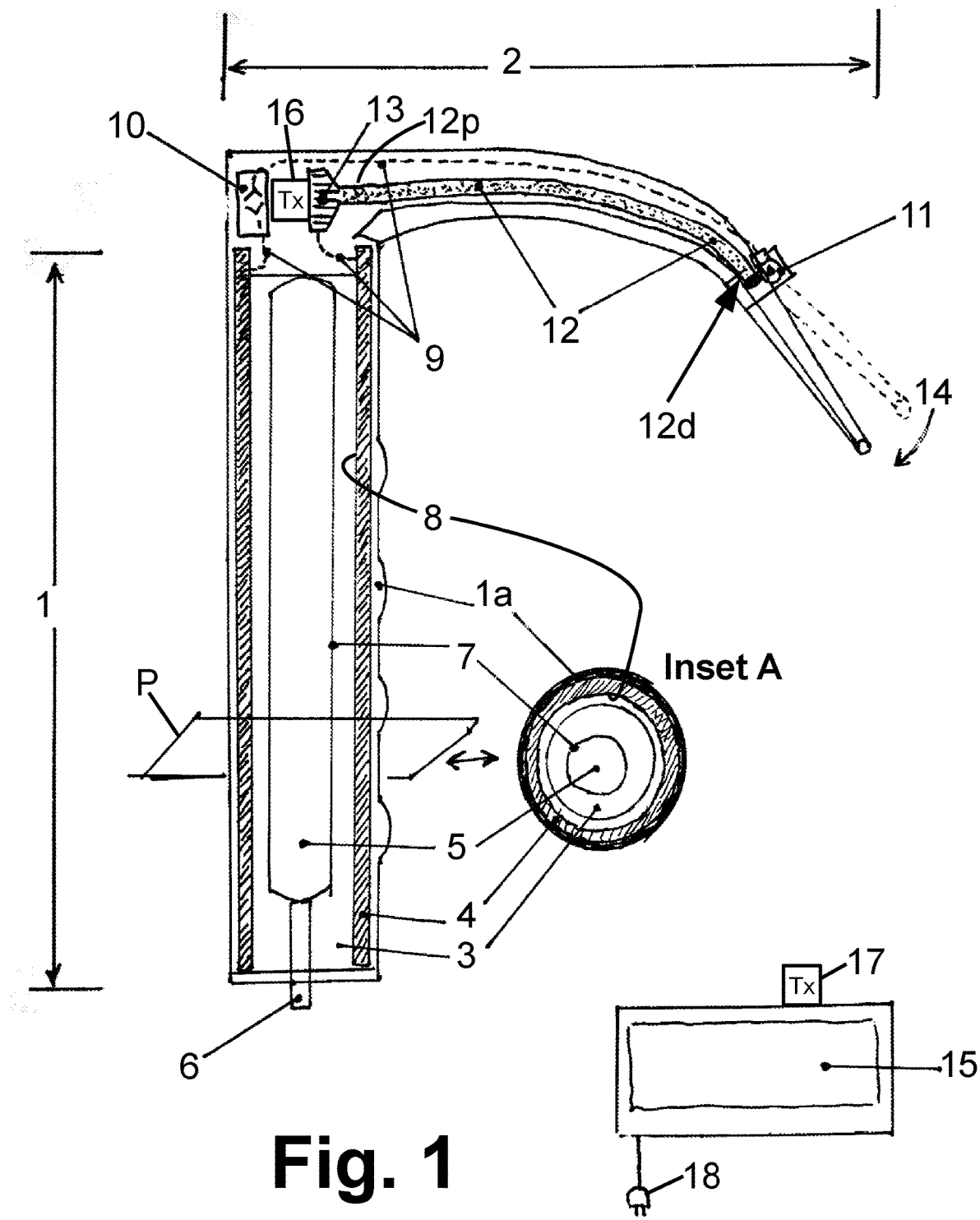
FIG. 1 diagrammatically shows a video laryngoscope including an electrical power supply comprising a chemiluminescent light source coupled with a bank of photovoltaic cells.

Tracheal intubation procedures are very common. For example, in 2010 more than 30 million such procedures were performed in the United States. In most waste disposal jurisdictions (including in the United States), the laryngoscope blade after use must be treated as infectious medical waste, since it mates with a mucous membrane of the patient. The handle, on the other hand, does not come into contact with mucous membranes, and hence may not be considered infectious waste but is a significant vector for contamination of work surfaces between patient care encounters. In some commercial laryngoscope designs, the laryngoscope is a one-piece unit in which the handle is integrally formed with the blade, e.g. as a one-piece molded plastic device. In such designs, the laryngoscope is often a single-use disposable item. In other commercial laryngoscope designs, the blade is detachable from the handle, and may be a durable item (e.g., sterilized by autoclaving between patients). Even in a two-piece design, however, the laryngoscope may still be treated as a single-use disposable item, an advantage being that the handle can be disposed of separately as ordinary waste and thereby reducing the total volume of infectious waste to be processed by the hospital.

In most regulatory jurisdictions, the battery disposed in the handle (to power the lamp) is considered a type of recyclable and/or hazardous waste, although it is not infectious waste. Hence, the battery must be disposed of in accordance with jurisdictional regulations and/or environmentally conscious healthcare system initiatives governing battery disposal, which are different from the regulations governing disposal of infectious waste. This means that after using the laryngoscope, the battery must be removed and disposed of in a regulatory-compliant battery disposal receptacle, separately from the disposal of the laryngoscope in the infectious waste receptacle (and, optionally, the handle in ordinary waste in the case of a separable two-piece design).

While the extra step of disposing of the battery may seem inconsequential, in practice it is troublesome in a surgical setting. The advantages of a single-use disposable laryngoscope include simplicity and the assurance that the battery is fully charged at the start of the laryngoscopy procedure. However, the need to remove the battery along with placing the single-use disposable laryngoscope (or at least its blade) into the infectious waste receptacle means that the surgical operating room must be equipped with a compliant battery disposal receptacle and personnel. Moreover, the battery can lose charge during storage, leading to inadequate illumination and potential intubation failure. Battery powered electric lamps can also be prone to unreliability due to intermittent electrical contacts, which can lead to sudden and complete loss of illumination, potentially during the tracheal intubation process. These issues can introduce delays in the surgical procedure, which is undesirable in many clinical settings in which the surgical operating room is scheduled for a number of surgical sessions in a given day with only short intervals allocated between surgical sessions, and can also lead to undesirable patient outcomes, patient injury or even death. Furthermore, eliminating batteries as a power source for disposable medical devices, such as laryngoscopes, has a potential of saving 10-30 million batteries from becoming environmental hazards via improper dumping or lack of recycling, as well as reducing the added costs associated with proper disposal by medical facilities. Additionally, a laryngoscope design that eliminates integral power supply by displacement to a fully reusable and remote power supply, that does not become infectious waste, results in fully disposable infectious waste instrument. By this action, the single use, infectious waste laryngoscope can be considered for single use medical device reprocessing by various medical device manufacturers potentially lowering overall costs for elective intubation procedures.

Laryngoscope designs have been described in which a chemiluminescent light source replaces the battery. However, in this design the optical output power of the chemiluminescent light source would need to be sufficiently high (i.e., sufficiently bright) to provide sufficient illumination for visual observation of the glottis of the patient when the laryngoscope blade operatively engages the tongue of the patient. In one described design (Cantele, U.S. Pat. No. 5,277,173), the chemiluminescent light source is disposed in the laryngoscope blade. While this advantageously places the chemiluminescent light source in close proximity to the distal end of the blade, it requires some modification (and likely enlargement) of the blade in order to accommodate the integration of the chemiluminescent light source into the blade. These considerations may also limit the size of the chemiluminescent light source, which will lower the optical output power. In other designs (Weinmann, Intl Pub. WO 2019/032459 A1) the chemiluminescent light source is disposed in the handle and a light conduit is provided to convey the chemiluminescence to the distal end of the blade. This approach may allow for a larger chemiluminescent light source, but the light conduit introduces optical losses, especially at the optical coupling of the light conduit to the chemiluminescent light source.

On the other hand, video laryngoscopes are commercially available. A video laryngoscope contains an on-board camera, and is typically connected with a separate video monitor by a cable. This allows the camera and light source of the video laryngoscope to be powered via the connection cable, which is also used to transmit video from the camera to the separate video monitor. The blade-mounted camera is positioned to directly observe the glottis of the patient when the laryngoscope blade operatively engages the tongue of the patient. However, the camera can complicate design of the blade. Moreover, most tracheal intubation procedures are straightforward, and can be performed by a competent anesthesiologist in less than one minute. For such routine procedures, employing a video laryngoscope can actually slow down the procedure, as the connecting cable must be connected between the video laryngoscope and the monitor, and that cable can physically interfere with the anesthesiologist or other surgical personnel. The cable can also interfere with manipulation of the laryngoscope and can be prone to connection failure after prolonged use.

With reference to FIG. 1, a video laryngoscope is disclosed. The laryngoscope includes a handle 1 and a laryngoscope blade 2. The handle 1 may be integral with, or separate from, the blade 2. The laryngoscope blade 2 connects with the handle 1 at a proximal end of the blade 2, while a distal end 14 of the blade 2 is sized and shaped to operatively engage the tongue of a patient to assist an anesthesiologist in performing a tracheal intubation (or, more generally, to facilitate viewing the glottis of the patient by way of the distal end 14 of the laryngoscope blade 2 operatively engaging the tongue of the patient to move it out of the way).

The handle 1 is hollow, having an exterior wall 1a made of, for example, hard polycarbonate/acrylic (although other materials, including metal, are contemplated for the exterior wall 1a). The handle 1 is shown in sectional view in FIG. 1 (as well as in the other drawings herein). Furthermore, Inset A shows a cross-sectional view of the handle 1 at the indicated cross-section plane P. A chemiluminescent light source is provided inside the hollow handle 1. The chemiluminescent light source includes a first reactant fluid 3 disposed in a first container 8, and a second reactant fluid 5 disposed in a second container 7, which is fragile as will be described. Upon rupture of the fragile second container 7, for example by action of a plunger 6 that fractures the second container 7, the first and second reactant fluids 3, 5 combine and produce chemiluminescence. Optionally the mixing of the reactant fluids 3, 5 may be improved by shaking the laryngoscope after activating the plunger 6.

A bank of photovoltaic cells 4 are arranged around the periphery of the first container 8, which is optically transparent to the chemiluminescence. The photovoltaic cells 4 convert chemiluminescence generated by the reaction of the first and second reactant fluids 3, 5 into electrical power. Electrical wiring (or more generally, electrical conductors) 9 electrically connect the photovoltaic cells 4 to a power/voltage modulator/regulator (or, more generally, one or more power conditioning electrical components) 10 which condition the electrical power supplied by the photovoltaic cells 4 to power a light emitting diode (LED) 11 that is arranged on (or in) the blade 2 to illuminate the glottis of the patient when the distal end of the laryngoscope blade 2 operatively engages the tongue of the patient.

Additionally, the video laryngoscope of FIG. 1 includes an image sensor 13 disposed on the laryngoscope blade 2 or in the handle 1. As the image sensor 13 is typically used in acquiring video, a term such as "video sensor" may also be used herein to refer to the image sensor 13. (However, it is contemplated to also acquire one, two, or more still images using the sensor 13 for purposes such as documenting the intubation procedure). The image sensor 13 is powered by electrical power from the photovoltaic cells 4 delivered via the wiring 9. In one embodiment, the image sensor 13 is a CMOS image sensor, although an imaging sensor employing another imaging technology is contemplated. The image sensor 13 is configured to image the glottis of the patient when the distal end of the laryngoscope blade 2 operatively engages the tongue of the patient. The LED 11 provides the illumination light for this imaging. As seen in FIG. 1, the illustrative image sensor 13 is disposed at the proximal end of the blade 2. This does not provide the image sensor 13 with a direct view of the glottis. To address this, an image conduit 12 is provided. The image conduit 12 has a first (i.e. distal) end 12d disposed on the laryngoscope to view the glottis of the patient when the distal end 14 of the laryngoscope blade 2 operatively engages the tongue of the patient. The image conduit extends along at least a portion of the laryngoscope blade 2 and terminates at a second (i.e. proximal) end 12p that is operatively connected with the image sensor 13. The image conduit 12 is a rigid fiber optic rod, e.g. a fused optical fiber, that is designed to transmit a coherent image. Preferably, the rigid image conduit 12 is heated in order to be bent to conform with the curvature of the blade 2; after cooling, the conformally bent image conduit 12 regains its rigidity. It will be appreciated that an advantage of employing the image conduit 12 is that the image sensor 13 can thereby obtain high quality images of the glottis without requiring the image sensor 13 to be disposed closer to the distal end 14 of the blade 2 to directly view the glottis. This reduces or eliminates the need to modify the blade 2 to accommodate the image sensor 13, and allows for placement of the image sensor 13 at the proximal end of the blade 2 where there is more space to accommodate the image sensor 13. Furthermore, this proximal placement of the image sensor 13 reduces the length of the portion of the wiring 9 that connects the image sensor 13 to the photovoltaic cells 4. (It is contemplated to alternatively dispose the image sensor in the handle 1 near the proximal end of the blade, in which case the image conduit 12 would be bent in an arc to connect with the image sensor in the handle).

The image sensor 13 includes, or is operatively connected with, a radio transmitter 16 that wirelessly transmits images acquired by the image sensor 13 to a separate video monitor 15 (via a corresponding radio receiver 17 of the video monitor 15). Typically, the on-board radio transmitter 16 and the corresponding radio receiver 17 of the video monitor 15 are both transceivers, so as to allow pairing (i.e., defining of a dedicated wireless communication channel) of the laryngoscope and the video monitor 15. In a suitable embodiment, both transceivers 16, 17 are Bluetooth transceivers and employ conventional Bluetooth wireless transmission protocols. For example, by way of non-limiting illustration, transceivers employing Bluetooth Low Energy, i.e. Bluetooth LE or BLE, are particularly well suited for the transceivers 16, 17 due to the low power draw of BLE. The illustrative on-board radio transceiver 16 is operatively connected with the image sensor 13 so that it receives power from the photovoltaic cells 4 together with the image sensor 13. Alternatively, the radio transceiver 16 may be a separate component operatively connected with the image sensor, in which case additional wiring 9 is suitably provided to power the radio transceiver 16 using the photovoltaic cells 4. The on-board radio transceiver 16 may, by way of non-limiting illustration, comprise a microprocessor or IC with low power draw, such as an Advanced RISC Machine, i.e. ARM, processor. The separate video monitor 15 may be powered by an electrical plug 18, as shown, or by an on-board electrical battery. In a variant embodiment (not shown), it is contemplated to replace the separate video monitor 15 by an on-board video monitor that is mounted to the handle 1 or to the proximal portion of the blade 2, i.e. on the blade near its connection with the handle 1. In this variant embodiment, the on-board video monitor would be suitably powered by the photovoltaic cells 4. In some embodiments, the on-board video monitor would connect with the handle or proximal portion of the blade of the laryngoscope via a detachable connection, so that the on-board video monitor could be removed and reused.

In general, the video acquisition process involves acquiring successive images (i.e. frames) at a chosen frame rate, e.g. at 30 frame/second (i.e. 30 fps) in televised video although the video laryngoscope can operate at a different fps if desired. Each frame is acquired by the image sensor 13 and the image data making up the frame is transmitted from the image sensor 13 to the video monitor 15 via the paired transceivers 16, 17. The electronic processing involved in the video acquisition can be variously divided between on-board electronics of the image sensor 13 disposed in the laryngoscope and electronics of the video monitor 15. In one approach, the electronic processing is mostly performed at the video monitor 15, e.g. the video monitor sends trigger signals to the image sensor at the frame rate, and in response to reach received trigger signal the image sensor acquires a single image and sends it back to the video monitor which receives the images and constructs and displays the video stream. This approach advantageously reduces the electronic data processing power overhead of the image sensor 13, but may require the video monitor 15 to be a dedicated monitor designed specifically to operate with the laryngoscope. In other embodiments, the electronic processing is performed mostly by on-board electronics of the image sensor 13 disposed in the laryngoscope. In this approach, the on-board electronics of the image sensor 13 automatically acquire frames at the frame rate, converts the frames to a video stream in a video format (e.g. AVI, FLV, WMV, MOV, MP4, . . . ) and transmits the video stream to the video monitor. This approach entails higher processing power overhead at the image sensor 13, but makes the video laryngoscope compatible with standard video monitors that can receive a wireless video stream via Bluetooth or another wireless communication protocol.

In a suitable implementation of the laryngoscope of FIG. 1, the blade 2 has a design in the Macintosh style, but has an exaggerated curve at the distal ⅓ portion 14. This exaggerated curve permits the low power consumption LED 11 and an optional lens to be mounted in a manner that can improve the visual axis of observing the glottis during video laryngoscopy. The handle 1 contains two compartments 7, 8 housing to separate chemical reactant fluids 3, 5 separated by the breakable inner container 7 (containing the second reactant fluid 5) with the plunger 6 that fractures the inner container 7 when pressed. The internal aspect of the outer most portion of the hollow laryngoscope handle 1 is lined with the photovoltaic cells 4. As chemiluminescence is produced, electrical current begins to power the CMOS image sensor 13 and the Bluetooth transmitter 16 mounted at the proximal (base, close to the handle) portion of the blade 2. The electrical power generated by the photovoltaic cells 4 also powers the LED 11 (the same bank of cells powers both, or alternatively separate banks of photovoltaic cells are provided for powering the image sensor 13 and LED 11, respectively). The illustrative voltage regulator or modulator 10 connects to the LED by the electrical wiring or the like. The Bluetooth (or other wireless communication, such as WiFi or near field magnetic induction between transmitting and receiving coils at a pre-established communication frequency (in reverse direction from the frequency responsible for the magnetically induced power), distinct from the power producing frequency) capabilities send wireless video data to the nearby durable high-definition video screen and/or video processor 15. Note that the video monitor 15 is not shown to the same scale as the laryngoscope in FIG. 1.

The chemiluminescent light source is particularly well suited for use as the illumination source in a laryngoscope. A chemiluminescent light source is a single-use light source, which comports with its use in a single-use disposable laryngoscope. Furthermore, the chemiluminescent light source is typically not considered hazardous waste, as the chemicals employed can be chosen to be noncorrosive and non-toxic. As such, a single-use disposable laryngoscope employing a chemiluminescent light source can be disposed of as a unit in the infectious waste receptacle, without needing to remove the chemiluminescent light source before disposal. The chemiluminescent light source also maintains the simplicity of use of a single-use disposable laryngoscope. The chemiluminescent light source may be activated using the illustrative plunger 6, or by another activation mechanism such as squeezing the handle of the laryngoscope, or giving the laryngoscope a vigorous shake before use, depending upon the design.

There is a design tradeoff in designing the operating characteristics of the chemiluminescent light source. It is possible to design a chemiluminescent light source for higher intensity, at the cost of shorter operational lifetime, by suitable selection of the chemiluminescent fluids and the relative concentrations of the constituents of the chemiluminescent fluids. Hence, the chemiluminescent light source can optionally be optimized for a shorter operating lifetime of a few minutes or a few tens of minutes, thus allowing for designing it to provide higher intensity light output. However, this approach has limitations that will cancel out the advantages of relatively low cost, low heat and ease of disposability.

However, in the video laryngoscope of FIG. 1, the chemiluminescent light source effectively has its optical power increased by way of using the chemiluminescent light source to power the LED 11. As the photovoltaic cells 4 can surround most (or possibly all) of the exterior surface area of the first (outer) container 8, this means that most (or all) of the emitted chemiluminescent light impinges on the photovoltaic cells 4 and is therefore converted to electrical power with the conversion efficiency of the photovoltaic cells 4. Even with low cost crystalline silicon or thin-film photovoltaic cells, conversion efficiencies of 20% or higher are achievable, meaning that much of the power generated by the chemiluminescent light source is delivered to power the LED 11 and the image sensor 13 and radio transceiver 16. By contrast, laryngoscope designs to use a chemiluminescent light source to provide direct illumination of the glottis (by the chemiluminescence itself) may suffer substantial optical losses at the optical coupling between the chemiluminescent light source and the light conduit. Even in designs in which the chemiluminescent light source is disposed in the blade itself, optical losses can be high since most of the generated chemiluminescence is not directed toward the glottis.

As yet a further advantage, the nature of the chemiluminescent light source (a chemical reaction having a fixed reaction rate at atmospheric pressure and typical operating room temperature) ensures that the chemiluminescent light source will stay on for the design-basis operational lifetime. By contrast, a battery can lose charge over time when in storage, so that it may be insufficiently charged at the time of use, or can experience intermittent electrical contact failure during use.

Figure 2:
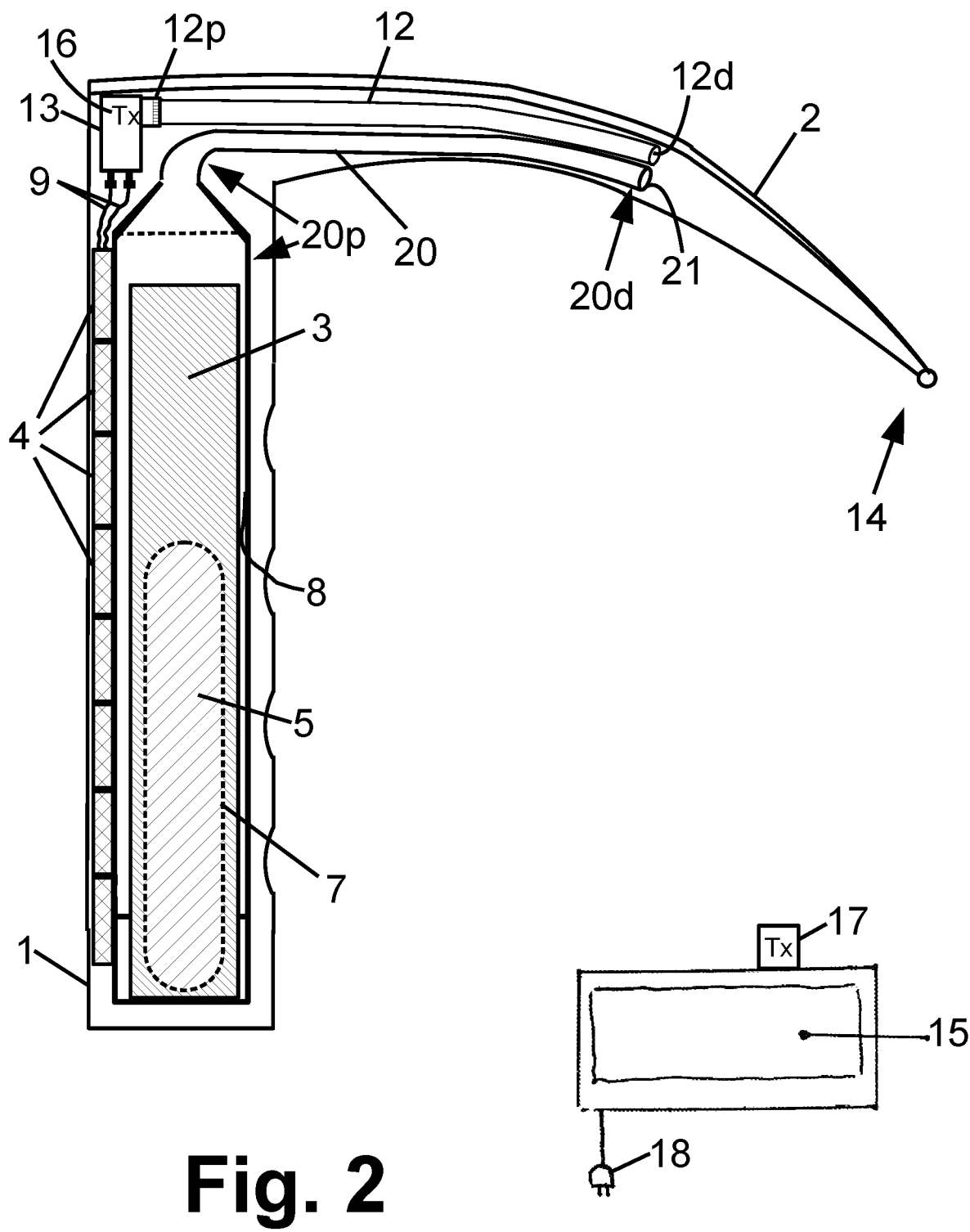
FIG. 2 diagrammatically shows a video laryngoscope including an electrical power supply comprising a chemiluminescent light source coupled with a bank of photovoltaic cells, in which the chemiluminescent light directly illuminates the procedure.

With reference to FIG. 2, another video laryngoscope is shown, which is similar to the laryngoscope of FIG. 1, and includes the handle 1, blade 2 with distal end 14, first and second reactant fluids 3, 5 in respective first and second containers 8, 7, and photovoltaic cells 4 optically coupled with the first container 8. (In FIG. 2, the photovoltaic cells 4 are shown on only one side of the first container 8, but can optionally fully surround the first container 8 as shown in more detail in FIG. 1 including Inset A). The laryngoscope of FIG. 2 further includes the electrical wiring 9, and the image sensor 13 with (here integral) radio transmitter 16 and optically coupled image conduit 12 as already described with reference to FIG. 1. The radio transmitter 16 communicates with the paired video monitor 15 via its transceiver 17, as previously described. The principal difference of the embodiment of FIG. 2 compared with that of FIG. 1 is that the LED 11 and associated power conditioning 10 of FIG. 1 is replaced by direct illumination by the chemiluminescence in the embodiment of FIG. 2. To this end, a light conduit 20 has a proximal end 20p that is optically coupled with the chemiluminescent light source, and the light conduit 20 extends along a portion of the laryngoscope blade 2 and terminates at a distal end 20d. In some embodiments, the light conduit 20 may provide sufficient collimation of the light to form the chemiluminescence into a light beam suitable for illuminating the patient's glottis when the blade 2 is operatively engaged. In other embodiments, at least one optical component 21, such as an illustrative lens 21, is optically coupled with the second, i.e. distal end 20d of the light conduit 20 in order to form light exiting from the second end 64 of the light conduit into illumination for illuminating the patient's glottis. The lens 21 may be a simple lens, or may be a compound lens, Fresnel lens, collimating reflector, or other optical component or combination of optical components suitable for forming the beam. In some embodiments, the optical component 21 may be integrally formed with the distal end 20d of the light conduit 20, for example by heating the distal end 20d of the light conduit 20 (assumed here to be a heat-formable plastic) to cause it to ball up and form a simple lens.

As previously noted, using the chemiluminescence to directly illuminate the glottis can be problematic due to poor light coupling of the chemiluminescent light source into the light conduit. In the embodiment of FIG. 2, this is addressed by forming (the proximal end 20p of) the light conduit 20 to extend into the handle 1, and embedding the chemiluminescent light source in the portion of the light conduit 20 extending into the handle 1. This maximizes the light coupling.

Furthermore, in the embodiment of FIG. 2 it is not necessary for the chemiluminescence to illuminate the glottis well enough for the anesthesiologist to observe the glottis. Rather, it merely must be sufficient to obtain video of the glottis using the image sensor 13. As the image sensor can have much higher light sensitivity than the human eye, the optical power requirements are thereby reduced. Hence, in some embodiments, the optical output power of the chemiluminescent light source is not effective to provide illumination via the light conduit 20 for visual observation of the glottis of the patient when the laryngoscope blade 2 operatively engages the tongue of the patient; but, the optical output power of the chemiluminescent light source is effective to provide illumination via the light conduit 20 for observation of the glottis of the patient via the image sensor 13 when the laryngoscope blade 2 operatively engages the tongue of the patient.

(Similarly, in FIG. 1, the LED 11 need only be bright enough to provide illumination for the image sensor 13 to observe the glottis. Hence, in some embodiments the optical output power of the LED 11 is not effective to provide illumination for visual observation of the glottis of the patient when the laryngoscope blade 2 operatively engages the tongue of the patient; but, the optical output power of the LED 11 is effective to provide illumination for observation of the glottis of the patient via the image sensor 13 when the laryngoscope blade 2 operatively engages the tongue of the patient.)

To further illustrate, the minimum laryngoscope illumination standard for visual observation of the glottis of the patient has been set at 500 lux by the ISO 7376:2009 standard. This value considered to be the minimal optimum illumination level for direct laryngoscopy and tracheal intubation. However, the ISO 7376:2009 standard does not consider individualized preferences, skill levels, experience and conditions, and applies for direct visual observation of the glottis by the anesthesiologist. A study investigating visual acuity at 50 lux, 200 lux, 700 lux, and 2000 lux found that visual acuity is lower at 50 lux than at 200 lux, continues to improve at 700 lux, with no further improvement observed at 2000 lux. See Baker et al., "Visual Acuity During Direct Laryngoscopy at Different Illuminance Levels", Anesthesia-Analgesia vol. 116 no. 2, pp. 343-350

(February 2013). This study also found that the average observation distance for direct laryngoscopy is 32 cm.

Currently available chemiluminescent light sources are unable to provide illumination of 500 lux as required by current ISO standards for direct laryngoscopy. To the contrary, the illuminance produced by a chemiluminescent light source at a distance of 32 cm (the average observation distance for direct laryngoscopy), is expected to be less than 10 lux. Thus, it is recognized herein that employing a chemiluminescent light source as the illumination source in a laryngoscope is expected to be feasible only if the chemiluminescent light source is used in combination with the image sensor 13, e.g. in a video laryngoscope.

Advantageously, an illumination of 200 lux or less, or even 50 lux or less, at a video sensor distance of 2-3 cm is expected to be sufficient for video laryngoscope operation due to the higher sensitivity of the image sensor 13 compared with the acuity of direct visual observation, and the closer placement of the image sensor 13 (e.g. 2-3 cm) during video laryngoscopy compared with the larger distance of the human eye (e.g., 32 cm) during direct laryngoscopy. Laryngoscope embodiments disclosed herein achieve this by a synergistic combination that uses a sensitive, photoelectric powered video sensor and low level illumination (e.g., 200 lux or less at an image sensor distance of 2-3 cm, or in some embodiments 50 lux or less at an image sensor distance of 2-3 cm. This low-level illumination is provided directly by the chemiluminescent light source (e.g. FIG. 2) or indirectly by an LED photoelectrically powered by the chemiluminescent light source (e.g. FIG. 1). Thus, laryngoscope embodiments disclosed herein are highly effective, disposable and convenient for use in tracheal intubation for routine anesthesia and all procedures requiring tracheal intubation.

As another variant (not shown) of the embodiment of FIG. 1, it is contemplated to provide a laryngoscope substantially similar to that of FIG. 1, but omitting the image conduit 12, image sensor 13, separate video monitor 15, and associated radio transceivers 16, 17. This embodiment is then not a video laryngoscope. As already discussed with reference to FIG. 1, employing the LED 11 powered by the power device comprising the chemiluminescent light source and coupled photovoltaic cells 4 has substantial advantages over attempting to provide human-visible illumination of the glottis using direct chemiluminescence as the illumination. The chemiluminescent light source effectively has its optical power increased by capturing more of the chemiluminescence via the (mostly or completely) surrounding bank of photovoltaic cells 4. Furthermore, the LED 11 can be designed to output white light whose color spectrum is optimized for visual observation of the glottis, e.g. having desired spectral characteristics (color rendering index, CRI, et cetera). In some embodiments, the LED 11 is contemplated to be designed to illuminate the glottis with both visible light and ultraviolet light, e.g. in the ultraviolet range of 300-450 nm. While the human eye is relatively insensitive to this deep-bluish to ultraviolet range, the ultraviolet light component can stimulate phosphorescence of the vocal cords, thereby increasing their visibility. (This emission of ultraviolet light is also contemplated to be employed in conjunction with the image sensor 13, which may optionally be tuned to detect in the ultraviolet).

In any of the foregoing embodiments, the laryngoscope blade 2 is connected with the handle 1 to form the laryngoscope. In a two-piece laryngoscope design the blade is detachable from the handle, in which case the laryngoscope blade 2 is connectable with the handle 1 to form the laryngoscope. In a one-piece design the laryngoscope blade 2 and the handle 1 are integrally formed. The laryngoscope blade 2 is specially configured for use in a laryngoscopy procedure, and may for example be a curved Macintosh laryngoscope blade (as shown) or a straight (or straighter) Miller laryngoscope blade, although more generally any laryngoscope blade design suitable for clinical use may be employed. It is also contemplated for the laryngoscope blade to include a tube guide (not shown) for guiding a tracheal tube, or other features known in the laryngoscopy arts to be of clinical benefit for specific medical procedures. The handle 1 is sized and shaped for the anesthesiologist (or other user) to hold, and the blade 2 is connected with (or connectable with) the handle 1 in an orientation that facilitates its use in facilitating looking inside the patient's pharynx to view the larynx, vocal cords, and glottis, and in one common application for its use in performing the maneuver in which the laryngoscope blade 2 is inserted into a patient's mouth, and is used to move the tongue and epiglottis aside to provide an unimpeded view of the patient's glottis so as to enable insertion of a tracheal tube. The illustrative laryngoscope blade 2 is mounted with the blade 2 oriented perpendicular to the handle 1, although as seen in FIG. 1 the illustrative curved Macintosh blade 2 is seen to progressively curve further away from perpendicularity with increasing distance away from the handle 1.

The illustrative laryngoscope employs the plunger 6 to activate the chemiluminescent light source. However, other activation mechanisms are contemplated, such as spring-loading the plunger 6 which may provide a more reliable activation of the chemiluminescent light source. In another contemplated approach, a protrusion (not shown) extends inward from the inside wall 1a of the handle, so that squeezing the handle causes the protrusion to rupture the fragile second container 7. In another contemplated approach, a weight (not shown) is disposed in the first container 8, or the second container 7 is movable within the first container 8, so that shaking the laryngoscope causes the fragile second container 7 to rupture due to impact of the weight or impact of the second container directly onto the first container. As yet another contemplated approach, a twist-type or bending-type activation mechanism could be employed, such as is commonly used in chemiluminescent glow sticks such as are used in children's toys and single-use light beacons of the type used in nighttime traffic management. In designing the activation mechanism consideration should be given to the need for the handle 1 to be sufficiently rigid to serve its primary purpose as the hand-hold via which the anesthesiologist manipulates the laryngoscope blade 2 to move the tongue and epiglottis aside in order to provide an unimpeded view of the patient's larynx and tracheal opening and enable insertion of a tracheal tube.

The first reactant fluid 3 and the second reactant fluid 5 can be any suitable combination of reactants that, when reacted together, generate chemiluminescence suitable for illuminating the glottis during a laryngoscopy procedure. In one suitable formulation the first reactant fluid (or, alternatively, the second reactant fluid) comprises hydrogen peroxide, and at least one of the first reactant fluid or the second reactant fluid comprises one or more fluorophores. The first container 8 optionally further includes at least one additional fluorophore disposed on an inner wall of the first container 8. A fluorophore is the chemical group or structural domain of the fluid that is responsible for the fluorescent light output when the two reactant fluids are mixed. (Note, the terms "fluorophore" and "dye" are used interchangeably herein to designate the chemical constituent or constituents that emit light in the chemiluminescence reaction). In one specific example, the first reactant fluid comprises hydrogen peroxide and the second reactant fluid comprises diphenyl oxalate and one or more fluorophores. Reaction of the hydrogen peroxide and diphenyl oxalate upon rupture of the second container generates an intermediate reactant which reacts with and excites the dye molecules to generate the chemiluminescence. The reaction rate is pH-dependent, and a weak base is optionally added to the second reactant fluid to speed up the reaction and increase the light intensity (albeit at the cost of a shorter duration of illumination, but this is acceptable since most tracheal intubation procedures only take a few minutes or less). In one embodiment, the fluorophore(s) output white light. This can be achieved by having multiple fluorophores, e.g. having peak emission at different wavelengths spanning the visible wavelength range. For example, the fluorophore 9,10-Bis(phenylethynyl)anthracene (BPEA) emits at a peak wavelength of 486 nm, the fluorophore rubrene emits orange-yellow at 550 nm, and the fluorophore violanthrone emits orange light at 630 nm, so that a suitable combination of these dyes produces white light. Some other suitable white chemiluminescent light sources are described in Dugliss, U.S. Pat. No. 4,678, 608 and Koroscil, U.S. Pat. No. 4,717,511, both of which are incorporated herein by reference in their entireties. Light intensity enhancement may also be obtained by the addition of metallic nanoparticles to one or both fluids. See Ray et al., "Aluminum Nanostructured Films as Substrates for Enhanced Fluorescence in the Ultraviolet-Blue Spectral Region", Anal Chem vol. 79 no. 17, pp. 6480-87 (2007); Asian et al., "Metal-Enhanced Chemiluminescence: Advanced Chemiluminescence Concepts for the 21$^{st}$ Century", Chem Soc Rev. vol. 38 no. 9, pp. 2556-64 (2009). These are merely non-limiting illustrative examples, and it is contemplated to employ any suitable fluorophore(s), including proprietary fluorophores, and optional additives.

In the example of FIG. 1, the chemiluminescence does not directly provide human-viewable illumination of the glottis. Consequently, the first and second reactant fluids 3, 5 can be designed to output light whose spectrum optimally couples with the photovoltaic cells 4. This provides much greater flexibility to design the chemiluminescent light source for high optical output power, as compared with laryngoscope designs to employ chemiluminescence to provide human-viewable illumination of the glottis. In the case of FIG. 2, the chemiluminescence does directly provide the illumination—but that illumination is "observed" by the image sensor 13, rather than being viewed by a human. As such, the spectrum of the chemiluminescence can again be designed to optimally match sensitivity of the image sensor 13.

The LED 11 in the embodiment of FIG. 1 may, for example, be a blue- or ultraviolet-emitting gallium nitride (GaN)-based photodiode coated with a white phosphor, or coated with a yellow phosphor of a thickness effective to allow a portion of blue direct GaN emission through so as to form white light. In some embodiments, the direct GaN emission includes an ultraviolet spectral component in the range of 350-450 nm, some of which passes through the phosphor layer to stimulate phosphorescence of the vocal cords, thereby increasing their visibility. However, since the LED light is viewed by the image sensor 13, rather than by a human, the spectrum of light output by the LED can be designed to optimally match sensitivity of the image sensor 13.

The embodiments of FIGS. 1 and 2 use the chemiluminescent light source to generate electrical power to drive the image sensor 13 and (in the embodiment of FIG. 1) the LED 11. However, other electrical power devices are contemplated.

For example, as shown in FIG. 3 which again shows a laryngoscope with the handle 1 and the laryngoscope blade 2 as previously described, the electrical power device may be a near field magnetic induction device. In this approach, an electromagnetic coil 22 is disposed inside the handle 1, and electrical conductors 24 connect to the electromagnetic coil 22 to power the image sensor 13 (for example, a CMOS image sensor) and the LED 11 (e.g., a 3 mm white LED) of FIG. 3. To induce the electric current in the electrical receiver coil 22, a radio frequency (RF) power generator 26 is provided, which is separate from the handle 1 and separate from the laryngoscope blade 2. The illustrative RF power generator 26 is a transmitting electromagnetic coil 26. The RF power generator 26 generates RF power that inductively couples with the coil 22 thereby inducing the electrical current in the electromagnetic coil 22 by near-field magnetic induction. To limit radio frequency interference, it is desirable for the RF power generator 26 to have low RF power output. To this end, the RF power generator 26 may be located close to the handle, e.g. as a compact unit disposed underneath the head or neck of the patient P. The RF power generator 26 is driven by drive electronics 28, for example an analog RF driver circuit, or a digital processor with associated digital-to-analog conversion. The illustrative drive electronics 28 are powered via an electrical power plug 30, such as a conventional 110V AC power plug. Alternatively, the drive electronics 28 may be powered by an on-board battery, such as a lithium-ion battery.

Figure 3:
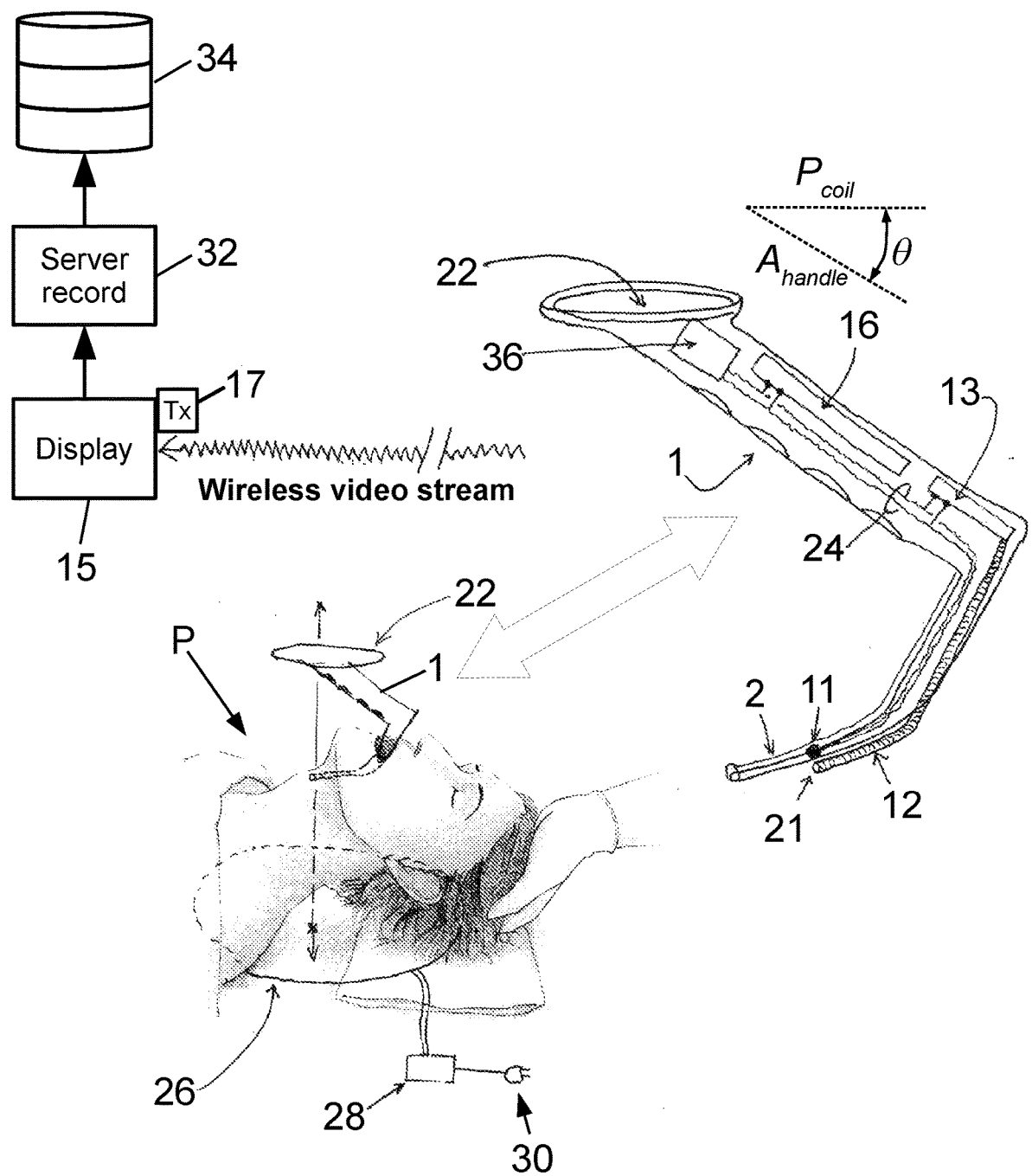
FIG. 3 diagrammatically shows a video laryngoscope system including

The illustrative laryngoscope of FIG. 3 otherwise has a configuration similar to that of FIG. 2, including the image sensor 13 optically coupled with the image conduit 12 (for example, a plastic light conduit of fiber optic) with the illustrative lens 21 or other optical component(s) disposed at the distal end of the image conduit 12. The previously described radio transmitter 16 (e.g., a WiFi, Bluetooth transmitter or near-field magnetic induction) transmits the video acquired by the image sensor 13 to the previously described radio receiver 17 for display on the previously described video monitor or display 15. In addition to displaying the image (e.g., of the glottis during an intubation procedure), the acquired video (or selected video frames) may be formulated as a server record 32 that is stored in a long term storage 34, e.g. a non-transitory storage medium such as a magnetic disk or array (e.g., a RAID) of magnetic disks and/or solid state drive (SSD) units, or so forth. See FIG. 4 and related discussion for some ways such records of laryngoscope procedures may be beneficially utilized.

In the embodiment of FIG. 3, the on-board image sensor 13, LED 11, and radio transmitter 16 of the laryngoscope are all powered by RF power received at the receiver coil 22 from the RF power generator 26 by near field magnetic induction. The RF power is preferably at a frequency that is high enough for efficient near field magnetic induction and low enough to avoid creating RF interference that might interfere with other electronics used in the operating room. In some non-limiting illustrative embodiments, the transmitting coil 26 is contemplated to be driven at a frequency of 500-1000 kHz. In some embodiments, the RF frequency is chosen in accord with the current Wireless Power Consortium (WPC) standard which uses a frequency 110-205 KHz, or the Alliance for Wireless Power (A4WP) whose standard is 6.78 MHz. These are merely non-limiting illustrative examples. Both the transmitting coil 26 and the receiver coil 22 are designed to be resonant at the same chosen RF frequency, that is, at a single RF frequency that used for the RF power transfer by near field magnetic induction. A power modulation unit 36, optionally controlled by a digital processor, preferably converts the RF power received at the receiver coil 22 to direct current or lower frequency alternating current electricity conditioned to power the on-board components 11, 13, 16. In some embodiments, the power modulation unit 36 comprises a power management integrated circuit (PMIC).

The receiver coil 22 is disposed in the handle 1. In the illustrative example of FIG. 3, the coil 22 has diameter that is comparable with the diameter of the handle 1. Making the coil 22 of large diameter provides a large area coil for receiving the RF power. The coil 22 is inside the handle 1 at least insofar as it is covered by an exterior epoxy or other electrical insulation such as epoxy coated magnetic wire to avoid the potential for the anesthesiologist contacting the bare metal with his or her hands when holding the handle 1. While the illustrative coil 22 is shown as a single turn, it is contemplated to employ a multi-turn coil as the receiver coil 22. In general, the induced voltage magnitude is expected to scale approximately linearly with the number of turns of the coil, coil diameter and coil depth or thickness. It is contemplated that the receiving coil will be optimized with regards to coil design, shape and construction in order to produce the appropriate voltage and current to supply all electrical component(s) of the specific laryngoscope embodiment, that being either video laryngoscope or direct visual laryngoscope.

The illustrative laryngoscope of FIG. 3 is a video laryngoscope that employs the image sensor 13 for video acquisition and the LED 11 to provide illumination. However, more generally any type of laryngoscope can employ electrical power delivered in real-time via near field magnetic induction during an intubation procedure, as described above. For example, if the ambient light is sufficiently high then the LED 11 may optionally be omitted. In another example, the laryngoscope employing real-time power received via near field magnetic induction may be a direct observation laryngoscope (that is, not a video laryngoscope) that omits the image sensor 13 and employs the LED 11 with sufficient brightness to enable direct observation of the glottis by the anesthesiologist during an intubation procedure. In any laryngoscope (video or direct) employing the LED 11, it is contemplated to include a light conduit and/or lens similar to the image conduit 12 and lens 21 of the imaging system but coupled to carry and direct light from the LED 11 into the glottis.

Generalizing the embodiment of FIG. 3, the handle 1 of the laryngoscope includes the receiving coil 22 for inducing electrical power in the laryngoscope when introduced into a magnetic field generated by the transmitting coil 26. The receiving coil 22 is located on or in the handle 1 in such a manner to be integral as a part of the structure of the handle itself through the manufacturing process. Generally, the coil support structure may also function as an ergonomic support for the operator's hand while using the instrument. The receiving coil 22 is preferably positioned to undergo efficient induction of electric current in the coil 22 to power the laryngoscope while in use. Optimal alignment is typically such that the receiving coil 22 is aligned in a parallel plane with the transmitting coil 26 when the transmitting coil 26 is placed underneath the head and/or neck of the patient P and the laryngoscope blade 2 is operatively engaged with the tongue of the patient P, although some deviation from this ideal orientation can occur without the laryngoscope losing electrical power. Advantageously, with the neck and head of the patient P in standard position for intubation, the transmitting coil 26 placed under the head and/or neck of the patient P, and the laryngoscope blade 2 operatively engaged with the tongue of the patient P, the orientation of the laryngoscope relative to the transmitting coil 26 in space is largely fixed, with only small variations in the position of the laryngoscope occurring during the intubation procedure or between patients. As indicated in FIG. 3, an angle θ can be defined between the plane $P_{coil}$ of the receive coil 22 and the axis of the handle $A_{handle}$. In some preferred embodiments, the angle θ is between 10 degrees and 50 degrees inclusive which provides for the two coils 22, 26 being at least close to parallel during intubation, although a larger or smaller angle is contemplated. In the case of the coil 22 being a multi-turn coil, the plane $P_{coil}$ suitably denotes the plane of each turn of the coil.

If the laryngoscope is a video laryngoscope as in FIG. 3, the handle 1 will contain a CMOS imaging sensor 13 or the like of low power consumption and sufficient frames per second for effective video wireless streaming to the receiving display 15 such as a monitor, tablet or smart-phone. Such a video stream is suitably accomplished utilizing a Bluetooth 24 Mbps (2.0-2.4 GHz), WiFi (>900 MHz) transmitter, or a magnetic induction transmission between receiving and transmitting electromagnetic coils at a frequency separate and distinct from the frequency used for the transmission of power to the laryngoscope, by way of non-limiting example. To avoid RF interference, transmitting and receiving coils preferably operate at a resonant frequency of <10 MHz or such frequency suitable for adequate power transfer to operate the laryngoscope. Overall power consumption of the laryngoscope is equivalent to its sum of electrical components. In the case of the direct, non-video capable laryngoscope, total power to operate a 3 mm white LED is about 50 mW at 2.8V. In the case of a video laryngoscope, power consumption will be higher in order to power the Bluetooth transmitter 16 (about 500 mW) and the CMOS image sensor 13 (about 3.2-21 mW at 30 frames/sec) and the LED 11 (50 mW). Reduction in power consumption may be feasible with a concurrent reduction in illumination if paired with a highly sensitive CMOS imager as there is a lack of ISO standardization of video laryngoscopes. There may also be additional power draw for operating ancillary components such as the power modulation unit 36.

The transmitting coil 26 may be of a variable size. In some non-limiting examples, the transmitting coil 26 is 25-80 centimeters in diameter, and more preferably about 18-20 inches in diameter (or other size dimension, e.g., if the transmitting coil is a square coil then each side of the square may preferably be about 18-20 inches), to provide a relatively large area of wireless power transfer activity and to accommodate variations in the positioning of the handle 1 containing the receiving coil 22. The illustrative transmitting coil 26 is positioned under the head and/or neck of the patient P, preferably with the center of the transmitting coil 26 being posterior and approximately at the level of the patient's larynx in a median sagittal anatomical plane. The power supply 28 for the transmitting coil 26 can in general be either AC volts or DC volts, and can be supplied by common wall electrical outlet 110V AC (e.g., via plug 30 in the illustrative embodiment) or by permanent or replaceable batteries. The transmitting coil 26 is preferably contained within an impermeable flexible synthetic material (e.g. a plastic) that is reusable for extended periods and multiple episodes, and easily decontaminated in the standard fashion of germicidal wipes used for the permanent pads or cushions of the operating room table. The transmitting coil 26 is suitably placed below the patient P under protective linens, and therefore does not come into direct contact with the patient P. For operating frequencies below about 10 MHz, adverse effects of RF exposure on the humans has not been documented. Some current recommendations establish RF head exposure of 8 W/Kg over a 6 minute time interval as an upper limit for acute exposure to magnetic fields in controlled environments. The transmitting coil 26 outputting power sufficient to drive the laryngoscope is expected to have an RF power output comparable to that of a cellular telephone and therefore presents no risk for adverse health effects or significant effect on implantable cardiac pacemaker or defibrillator devices as has been studied using Helmholtz coils.

The laryngoscope system of FIG. 3, including the laryngoscope comprising the handle 1 and blade 2, and the RF power generator 26, has numerous advantages. Because the electrical power is delivered in real-time via near field magnetic induction during an intubation procedure or other procedure utilizing the laryngoscope, there is no battery or other electrical power storage disposed in the laryngoscope (i.e., no battery or other electrical power storage in the handle 1 or in the blade 2). The receiver coil 22 can be made of any electrically conductive material such as a copper or stainless steel wire, and hence can be non-toxic and safely disposable. For a disposable laryngoscope, the elimination of the battery or other electrical power storage simplifies disposal as the battery does not need to be removed prior to disposal or reprocessing by a single use reprocessing medical device manufacturer. For a reusable laryngoscope, elimination of the battery or other electrical power storage simplifies sterilization of the laryngoscope between procedures, as again there is no battery to remove. Advantageously, the electromagnetic coil-powered laryngoscope of FIG. 3 can optionally be manufactured to be entirely impermeable, since there is no battery that needs to be removed during disposal or reprocessing. Having no battery in the laryngoscope makes the laryngoscope suitable for reprocessing, optionally as a "single-use" product. In this regard, medical facilities sometimes collect certain single-use devices and send them out to be re-processed for re-use. Some regulatory bodies, such as the Centers for Disease Control and Prevention (CDC) in the United States, allows this procedure as long as the re-processed device meets all standards of the original manufacturing.

Placement of the transmitting coil 26 underneath the head and neck of the patient P is convenient as the transmitting coil 26 in this placement does not interfere with other instruments, cabling, or the like that may be present and used in the operating room. In one contemplated embodiment, the transmitting coil 26 is embodied as a thin pliable plastic sheet with the metal coil embedded inside. The plastic sheet is easily cleaned and disinfected between procedures. In another contemplated embodiment, the transmitting coil 26 may be integrated into a headrest or into the operating table, e.g. forming a permanent or semi-permanent component of the operating table. While the illustrative transmitting coil 26 has a circular geometry, it is contemplated for the transmitting coil 26 to have another geometry that better conforms with a geometry of the pliable sheet, headrest, operating table, or other structure in which it is embedded or integrated. For example, a square or rectangular coil is also contemplated. (In such a geometry, the corners of the square or rectangular transmitting coil may optionally be rounded to facilitate manufacture and avoid sharp corners where higher electromagnetic field may be generated).

In general, the laryngoscope may be either a one-piece laryngoscope in which the blade 2 and handle 1 are integrally formed; or may be a two-piece laryngoscope in which the blade 2 is detachable from the handle 1. In a two-piece design, the wiring 9 suitably includes electrical connectors that mate together when the handle and blade are connected, and (in the embodiment of FIG. 2), the proximal end 20*p* of the light conduit 20 includes a suitable optical coupling that mates when the handle and blade are connected together. While the blade 2 may be a disposable or reusable design, the handle 1 of a two-piece design with the chemiluminescent light source may (depending on jurisdictional regulations) be fully disposable and considered non-infectious and non-hazardous waste. In general, the blade 2 may be made of a metal such as stainless steel, or a hard plastic such as polycarbonate or acrylic. Similarly, the handle 1 may be made of a metal such as stainless steel, or a hard plastic such as polycarbonate or acrylic.

Figure 4:
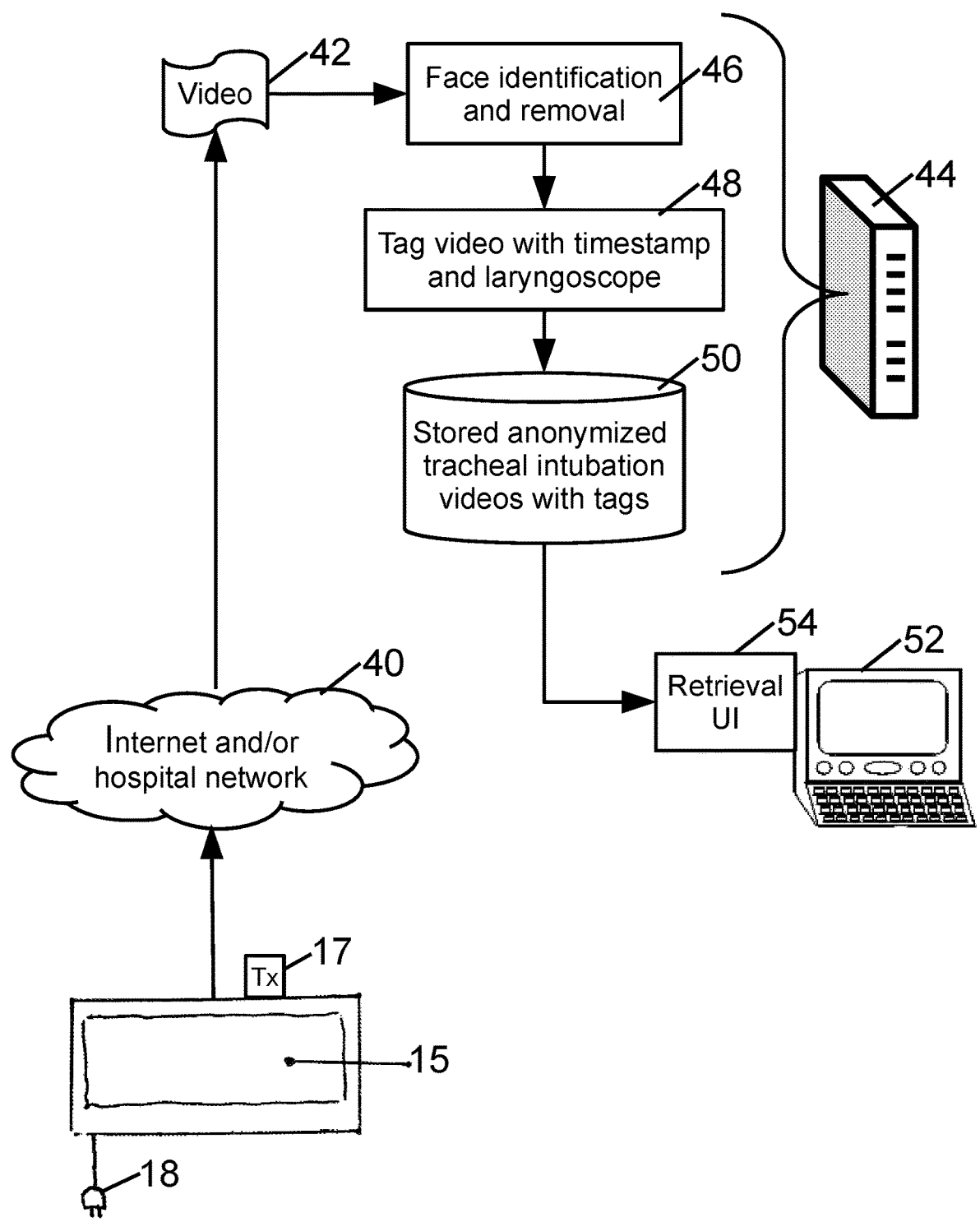
FIG. 4 diagrammatically shows a system for providing anonymized, auditable record of tracheal intubation procedures.

With reference now to FIG. 4, a system is disclosed which leverages a video laryngoscope to provide an auditable record of tracheal intubation procedures. As previously noted, in present practice an anesthesiologist typically has no evidentiary basis for defending against a dental- or vocal cord-related medical malpractice claim. Typically, video laryngoscopes do not record the acquired video, but merely display it on the video monitor. As a tracheal intubation is generally considered a routine procedure, no recordation is usually performed. The disclosed approach leverages the video laryngoscope to automatically record an anonymized record of each performed tracheal intubation. As already described with reference to FIGS. 1 and 2, the video monitor 15 receives and displays video acquired by the video laryngoscope. As further shown in FIG. 4, the video monitor 15 also has connectivity with the Internet and/or a hospital network (e.g. wired and/or wireless Ethernet, WiFi, and/or so forth) 40 and thereby sends the video 42 to a server computer 44. The server computer 44 thus connects with the video laryngoscope (here indirectly via the intermediary of the video monitor 15) to receive the video 42 from the connected video laryngoscope. The server computer 44 is programmed to perform an operation 46 in which face identification is performed on the video 42 and any frames of the video depicting a human face are removed to generate anonymized video. In the operation 46, the face identification merely identifies that a face is depicted in a frame—it does not then proceed to match that face with a particular person whose face is stored in a database, as in conventional facial recognition. Hence, the face identification 46 can employ any algorithm conventionally used in the first phase of facial recognition (the phase of identifying a face is present, e.g. by identifying landmarks such as eyes, nose, and mouth features). The reason for the operation 46 is that, as soon as the chemiluminescent light source is activated video starts to be recorded. Therefore, it is likely that the patient's face will be imaged as the video laryngoscope is moved toward the patient's mouth. Storing such images could constitute a violation of Health Insurance Portability and Accountability Act (HIPAA) regulations applicable in the United States, or other patient privacy regulations that may be applicable in other jurisdictions. In this regard, a "face" is not identified in the operation 46 in the case of a frame that only depicts the glottis of the patient (as when the distal end of the laryngoscope blade is engaged to perform the intubation), and is preferably also not identified in the case of a frame that only depicts the open mouth of the patient. These features are not sufficient to be "identifying" in most cases, and images of the open mouth prior to engagement of the laryngoscope may be needed to demonstrate the state of the patient's dental and/or oral features prior to commencement of the tracheal intubation procedure.

The server computer 44 is further programmed to perform an operation 48 in which the anonymized video is tagged with a video recording timestamp (for example, the video may be assigned a timestamp indicating when the video began to be recorded, and optionally also a time when the video recording stopped) and at least one of (i) a surgical location, and/or (ii) an anesthesiologist identifier. The surgical location may be variously specified. For example, the video monitor 15 may have a serial number and that serial number serves as the surgical location (insofar as the video monitor is owned by a single hospital at the time of the surgical procedure). In another approach, if the video monitor 15 has GPS capability then the surgical location may be specified by the GPS coordinates of the video monitor 15 acquired at the time of the video recording. The anesthesiologist identifier may be provided if, for example, the anesthesiologist is required to enter his or her name or employee number or other anesthesiologist identifier into the video monitor 15 when using it.

The server computer 44 is further programmed to store the anonymized video with the tags on a non-transitory storage medium 50 (e.g., a hard disk drive or other magnetic storage medium, or an optical disk or other optical storage medium, or a solid state drive or other electronic storage medium, or so forth). It should be noted that the server computer 44 may be a single computer, or may be a plurality of interconnected computers, e.g. a cluster of server computers or an ad hoc combination of server computers forming a cloud-based computing resource.

While the foregoing describes the processing and storage of anonymized video of a single tracheal intubation procedure, it will be appreciated that this process is repeated for each tracheal intubation procedure, and may optionally also be performed for a plurality of video laryngoscopes. Hence, the storage medium 50 may in general store a large number of tracheal intubation videos performed with a number of different video laryngoscopes by a number of different anesthesiologists. In most cases, the stored video is never retrieved.

If, however, a question arises as to a particular tracheal intubation procedure (for example, because a malpractice claim has been alleged respecting that particular tracheal intubation procedure), then the anonymized video for that particular tracheal intubation procedure can be retrieved at a workstation computer 52 running a suitable retrieval user interface (UI) 54 on the basis of the tagged timestamp and location and/or anesthesiologist. The retrieved video can then serve as video evidence for defending against the malpractice claim.

It should be noted that the system of FIG. 4 which leverages a video laryngoscope to provide an auditable record of tracheal intubation procedures can be used with any type of video laryngoscope that has Internet or network connectivity, or that is paired with a video monitor having Internet or network connectivity. Hence, it is not limited to video laryngoscopes of the designs of FIGS. 1 and 2.

The preferred embodiments have been illustrated and described. Obviously, modifications and alterations will occur to others upon reading and understanding the preceding detailed description. It is intended that the invention be construed as including all such modifications and alterations insofar as they come within the scope of the appended claims or the equivalents thereof.

The invention claimed is:

1. A laryngoscope comprising:
a handle including an electromagnetic coil;
a laryngoscope blade connected with the handle; and
one or more electrical components including at least one of a light emitting diode (LED) and/or an image sensor;
wherein the one or more electrical components are operatively connected to be powered by electrical current induced in the electromagnetic coil.

2. The laryngoscope of claim 1 wherein an angle ($\theta$) between a plane ($P_{coil}$) of the electromagnetic coil and axis ($A_{handle}$) of the handle is between 10 degrees and 50 degrees inclusive.

3. The laryngoscope of claim 1 wherein the laryngoscope does not include a battery.

4. The laryngoscope of claim 1 wherein the laryngoscope is a video laryngoscope and the one or more electrical components includes said image sensor and a radio transmitter configured to transmit video acquired by the image sensor.

5. The laryngoscope of claim 1 wherein the laryngoscope is a direct observation laryngoscope and the one or more electrical components includes said LED arranged to illuminate a glottis of a patient when the laryngoscope blade is engaged with a tongue of the patient.

6. A laryngoscope system comprising:
a laryngoscope as set forth in claim 1; and
a radio frequency (RF) power generator configured to induce the electrical current in the electromagnetic coil of the laryngoscope.

7. The laryngoscope system of claim 6 wherein the RF power generator includes:
A transmitting coil;
wherein the transmitting coil and the electromagnetic coil of the laryngoscope are resonant at a same RF frequency and the induction of the electrical current in the electromagnetic coil is at that same RF frequency.

8. The laryngoscope system of claim 7 wherein the transmitting coil is configured for placement underneath the head and/or neck of a patient.

9. The laryngoscope system of claim 7 wherein the transmitting coil is disposed in a plastic sheet.

10. The laryngoscope system of claim 7 wherein the transmitting coil is integrated into a headrest or into an operating table.

11. The laryngoscope system of claim 7 wherein the transmitting coil is planar and has a diameter of 25-80 centimeters.

12. The laryngoscope system of claim 7 wherein a plane of the electromagnetic coil of the laryngoscope is oriented parallel with a plane of the transmitting coil when the transmitting coil is placed underneath the head and/or neck of a patient and the laryngoscope blade is operatively engaged with a tongue of the patient.

13. The laryngoscope system of claim 6 wherein the laryngoscope is a video laryngoscope and the one or more electrical components includes said image sensor and a radio transmitter configured to transmit video acquired by the image sensor and the laryngoscope system further comprises:
a display configured to receive and display the transmitted video.

14. A laryngoscope comprising:
a handle;
a laryngoscope blade having a proximal end connected with the handle and a distal end that is distal from the handle;

an electrical power device comprising an electromagnetic coil disposed inside the handle and configured to emit electrical power comprising an electrical current induced in the electromagnetic coil disposed inside the handle; and at least one of a light source and/or an image sensor disposed on or in the laryngoscope and arranged to illuminate and/or view the glottis of an associated patient when the laryngoscope blade operatively engages the tongue of the associated patient, the light source and/or image sensor being connected to be powered by the electrical current induced in the electromagnetic coil disposed inside the handle.

15. The laryngoscope of claim 14 further comprising:
a radio frequency (RF) power generator configured to induce the electrical current in the electromagnetic coil disposed inside the handle.

16. The laryngoscope of claim 15 wherein the RF power generator comprises a transmitting coil configured for placement underneath the head and/or neck of the associated patient, wherein the transmitting coil and the electromagnetic coil disposed inside the handle are resonant at a same RF frequency.

17. A laryngoscopy method comprising:
engaging a tongue of a patient using a blade of a laryngoscope that further includes a handle with an electromagnetic coil; and while the blade is engaged with the tongue, inducing an electrical current in the electromagnetic coil by energizing a transmitting coil to generate RF power at a resonant frequency of the transmitting coil, wherein the electromagnetic coil is also resonant at the resonant frequency of the transmitting coil and the generated RF power is inductively coupled to the electromagnetic coil; and one of:
powering an image sensor and a radio transmitter of the laryngoscope by the electrical current induced in the electromagnetic coil to acquire and wirelessly transmit video of a glottis of the patient, or powering a light source of the laryngoscope by the electrical current induced in the electromagnetic coil to illuminate the glottis of the patient.

18. The laryngoscopy method of claim 17 further comprising:
prior to engaging the tongue of the patient using the blade of the laryngoscope, placing the transmitting coil underneath a head and/or neck of the patient.

19. The laryngoscopy method of claim 17 wherein the transmitting coil is integrated into a headrest or operating table, and the method further comprises:
prior to engaging the tongue of the patient using the blade of the laryngoscope, placing the head and/or neck of the patient on the headrest or operating table.

* * * * *